(12) United States Patent
Druzgala et al.

(10) Patent No.: US 6,864,279 B2
(45) Date of Patent: Mar. 8, 2005

(54) MATERIALS AND METHODS FOR TREATING COAGULATION DISORDERS

(75) Inventors: Pascal Druzgala, Santa Rosa, CA (US); Xiaoming Zhang, Campbell, CA (US); Jürg Pfister, Los Altos, CA (US)

(73) Assignee: Aryx Therapeutics, Santa Clara, CA (US)

( * ) Notice: Subject to any disclaimer, the term of this patent is extended or adjusted under 35 U.S.C. 154(b) by 0 days.

(21) Appl. No.: 10/132,750

(22) Filed: Apr. 24, 2002

(65) Prior Publication Data

US 2003/0199573 A1 Oct. 23, 2003

Related U.S. Application Data

(60) Provisional application No. 60/286,079, filed on Apr. 24, 2001.

(51) Int. Cl.[7] ............................................... A61K 31/35
(52) U.S. Cl. ....................... 514/457; 514/465; 549/285; 549/305
(58) Field of Search ................................. 549/305, 285; 514/457, 465

(56) References Cited

U.S. PATENT DOCUMENTS

| | | | |
|---|---|---|---|
| 3,325,515 A | 6/1967 | Schmitt et al. | |
| 4,748,185 A | 5/1988 | Entwistle et al. | |
| 5,686,486 A | 11/1997 | Yang et al. | |
| 5,856,525 A | 1/1999 | Li et al. | |

FOREIGN PATENT DOCUMENTS

| | | |
|---|---|---|
| FR | 2 765 579 A | 1/1999 |
| GB | 1 024 383 A | 3/1966 |
| GB | 1 032 253 A | 6/1966 |

OTHER PUBLICATIONS

Poupelin, JP, 'Pharmaceutical containing phthalide derivatives with antiinflammatory, antipyretic, and antalgic action' 1980 CA 92:110834.*

Masubuchi, M. '.beta.–(4–hyroxy–3–coumarinyl)–.beta.–substituted propionate' 1963 CA 59:75249.*

Ruan, Z, 'Study of sulfated .beta.–cyclodextrin chiral additive for enantiomeric separation by capillary electrophoresis' 1999 CA 131:303449.*

Avetisyan, AA, 'Synthesis and certain conversions of 3–(3, 3–dichloroallyl)–4–hydroxycoumarin' 1997 CA 128:48113.*

Svetlik, Jan, Vladimir Hanus and Juraj Bella (1993) "Expedient Synthesis of 3–Arylpropionic Acid Derivatives" *Synthetic Communications* 23(5):631–640.

Schmitt, Josef et al. (1966) "Sur un nouvel et puissant anticoagulant de synthèse" *Chemie Therapeutique* vol. I, p. 301–304. (In French).

Thaisrivongs, Suvit et al. (1995) "Structure–based Design of Novel HIV Protease Inhibitors: Carboxamide–Containing 4–Hydroxycoumarins and 4–Hydroxy–2–pyrones as Potent Nonpeptidic Inhibitors" *J. Med. Chem.* 38:3624–3637.

Zhao, He et al. (1997) "Coumarin–Based Inhibitors of HIV Integrase" *J. Med. Chem.* 40:242–249.

* cited by examiner

*Primary Examiner*—Amelia A. Owens
(74) *Attorney, Agent, or Firm*—Saliwanchik, Lloyd & Saliwanchik

(57) ABSTRACT

This invention is drawn to compounds which are more easily metabolized by the metabolic drug detoxification systems. Particularly, warfarin analogs which have been designed to include esters within the structure of the compounds are taught. The invention teaches methods of reducing the toxicity of drugs comprising the introduction of ester groups into drugs during the synthesis of the drug. This invention is also drawn to methods of treating coagulation disorders comprising the administration of compounds which have been designed to be metabolized by serum or intracellular hydrolases and esterases. Pharmaceutical compositions of the ester containing warfarin, analogs are also taught.

15 Claims, No Drawings

MATERIALS AND METHODS FOR TREATING COAGULATION DISORDERS

CROSS-REFERENCE TO RELATED APPLICATION(S)

This application claims the benefit of U.S. Provisional Application No. 60/286,079, filed Apr. 24, 2001.

BACKGROUND OF INVENTION

Warfarin (coumarin) is an anticoagulant which acts by inhibiting vitamin K-dependent coagulation factors. Warfarin based compounds are, typically, derivatives of 4-hydroxycoumarin, such as 3-(a-acetonylbenzyl)-4-hydroxycoumarin (COUMADIN). COUMADIN and other coumarin anticoagulants inhibit the synthesis of vitamin K dependent clotting factors, which include Factors II, VII, IX and X. Anticoagulant proteins C and S are also inhibited by warfarin anticoagulants. Warfarin is believed to interfere with clotting factor synthesis by inhibiting vitamin $K_1$ epoxide regeneration.

An anticoagulation effect is generally seen about 24 hours after administration and single doses of warfarin are effective for 2 to 5 days. While anticoagulants have no direct effect on an established thrombus and do not reverse ischemic tissue damage, anticoagulant treatment is intended to prevent the extension of formed clots and/or to prevent secondary thromboembolic complications. These complications may result in serious and possibly fatal sequelae.

Warfarin is typically used for the treatment of in patients suffering from atrial fibrillation. Such treatment reduces the incidence of systemic thromboembolism and stroke. The FDA has approved warfarin for the following indications: 1) the treatment or prophylaxis of venous thrombosis and pulmonary embolism, 2) thromboembolic complications associated with atrial fibrillation and/or cardiac valve replacement, and 3) reducing the risk of death, recurring myocardial infarction, and stroke or systemic embolism after myocardial infarction.

A number of adverse effects are associated with the administration of warfarin. These include fatal or nonfatal hemorrhage from any tissue or organ and hemorrhagic complications such as paralysis. Other adverse effects include paresthesia, headache, chest abdomen, joint, muscle or other pain, dizziness, shortness of breath, difficult breathing or swallowing, unexplained swelling, weakness, hypotension, or unexplained shock. Other adverse reactions reported include hypersensitivity/allergic reactions, systemic cholesterol microembolization, purple toes syndrome, hepatitis, cholestatic hepatic injury, jaundice, elevated liver enzymes, vasculitis, edema, fever, rash, dermatitis, including bullous eruptions, urticaria, abdominal pain including cramping, flatulence/bloating, fatigue, lethargy, malaise, asthenia, nausea, vomiting, diarrhea, pain, headache, dizziness, taste perversion, pruritus, alopecia, cold intolerance, and paresthesia including feeling cold and chills.

Drug toxicity is an important consideration in the treatment of humans and animals. Toxic side effects resulting from the administration of drugs include a variety of conditions which range from low grade fever to death. Drug therapy is justified only when the benefits of the treatment protocol outweigh the potential risks associated with the treatment. The factors balanced by the practitioner include the qualitative and quantitative impact of the drug to be used as well as the resulting outcome if the drug is not provided to the individual. Other factors considered include the physical condition of the patient, the disease stage and its history of progression, and any known adverse effects associated with a drug.

It is important to note that drug toxicity is an important consideration in the treatment of individuals. Toxic side effects resulting from the administration of drugs include a variety of conditions which range from low grade fever to death. Drug therapy is justified only when the benefits of the treatment protocol outweigh the potential risks associated with the treatment. The factors balanced by the practioner include the, qualitative and quantitative impact of the drug to be used as well as the resulting outcome if the drug is not provided to the individual. Other factors considered include the clinical knowledge of the patient, the disease and its history of progression, and any known adverse effects associated with a drug.

Drug elimination is the result of metabolic activity upon the drug and the subsequent excretion of the drug from the body. Metabolic activity can take place within the vascular supply and/or within cellular compartments or organs. The liver is a principal site of drug metabolism. The metabolic process can be broken down into synthetic and nonsynthetic ractions. In nonsynthetic reactions, the drug is chemically altered by oxidation, reduction, hydrolysis, or any combination of the aforementioned processes. These processes are collectively referred to as Phase I reactions.

In Phase II reactions, also known as synthetic reactions or conjugations the parent drug, or intermediate metabolites thereof, are combined with endogenous substrates to yield an addition or conjugation product. Metabolites formed in synthetic reactions are, typically, more polar and biologically inactive. As a result, these metabolites are more easily excreted via the kidneys (in urine) or the liver (in bile). Synthetic reactions include glucuronidation, amino acid conjugation, acetylation, sulfoconjugation, and methylation.

BRIEF SUMMARY

The subject invention provides materials and methods for safe and effective anticoagulant treatment. In a preferred embodiment, the subject invention provides therapeutic anticoagulant compounds. The compounds of the subject invention can be used to treat at-risk populations thereby bringing relief of symptoms, improving the quality of life, preventing acute and long-term complications, reducing mortality and treating accompanying disorders.

Advantageously, the subject invention provides compounds which are readily metabolized by the physiological metabolic drug detoxification systems. Specifically, in a preferred embodiment, the therapeutic compounds of the subject invention contain an ester group, which does not detract from the ability of these compounds to provide a therapeutic benefit, but which makes these compounds more susceptible to degradation by hydrolases, particularly serum and/or cytosolic esterases. The subject invention further provides methods of treatment comprising the administration of these compounds to individuals in need of anticoagulant treatment.

In a further embodiment, the subject invention pertains to the breakdown products which are formed when the therapeutic compounds of the subject invention are acted upon by esterases. These breakdown products can be used as described herein to monitor the clearance of the therapeutic compounds from a patient.

In yet a further embodiment, the subject invention provides methods for synthesizing the therapeutic compounds of the subject invention.

The subject invention provides materials and methods for the treatment of coagulation disorders. Specifically, the subject invention provides compounds which are readily metabolized by the metabolic drug detoxification systems. Specifically, this invention provides compounds which are susceptible to degradation by hydrolases, particularly serum and/or cytosolic esterases. This invention is also drawn to methods of treating coagulation disorders.

This invention is drawn to compounds which are more easily metabolized by the metabolic drug detoxification systems. This invention is also drawn to methods of treating coagulation disorders. Specifically, this invention provides analogs of drugs which have been designed to be more susceptible to degradation by hydrolases, particularly serum and/or cytosolic esterases and methods of treatment comprising the administration of these analogs to individuals.

DETAILED DISCLOSURE

The subject invention provides materials and methods for anticoagulant treatment. Advantageously, the therapeutic compounds of the subject invention are stable in storage but have a shorter half-life in the physiological environment than other drugs which are available for anticoagulant treatment; therefore, the compounds of the subject invention can be used with a lower incidence of side effects and toxicity.

In a preferred embodiment of the subject invention, therapeutic compounds are provided which are useful in providing anticoagulant treatment and which contain an ester group that is acted upon by esterases thereby breaking down the compound and facilitating its efficient removal from the treated individual. In a preferred embodiment the therapeutic compounds are metabolized by the Phase I drug detoxification system.

A further aspect of the subject invention pertains to the breakdown products that are produced when the therapeutic compounds of the subject invention are acted upon by esterases. The presence of these breakdown products in the urine or serum can be used to monitor the rate of clearance of the therapeutic compound from a patient.

The subject invention further provides methods of synthesizing the unique and advantageous therapeutic compounds of the subject invention. Particularly, methods of producing less toxic therapeutic agents comprising introducing ester groups into therapeutic agents (target drugs) are taught. The ester linkage may be introduced into the compound at a site that is convenient in the manufacturing process for the target drug. Additionally, the sensitivity of the ester linkage may be manipulated by the addition of side groups which hinder or promote the hydrolytic activity of the hydrolases or esterases responsible for cleaving the drug at the ester locus. Methods of adding such side groups, as well as the side groups themselves, are well known to the skilled artisan and can be readily carried out utilizing the guidance provided herein.

The subject invention further provides anticoagulant treatment comprising the administration of a therapeutically effective amount of esterified coumarin analogs to an individual in need of treatment. Accordingly, the subject invention provides esterified coumarin analogs and pharmaceutical compositions of these esterified compounds. In a preferred embodiment the patient is a human; however, animals also can be treated.

Adverse drug-drug interactions (DDI), elevation of liver function test (LFT) values, and QT prolongation leading to torsades de pointes (TDP) are three major reasons why drug candidates fail to obtain FDA approval. All these causes are, to some extent metabolism-based. A drug that has two metabolic pathways, one oxidative and one non-oxidative, built into its structure is highly desirable in the pharmaceutical industry. An alternate, non-oxidative metabolic pathway provides the treated subject with an alternative drug detoxification pathway (an escape route) when one of the oxidative metabolic pathways becomes saturated or non-functional. While a dual metabolic pathway is necessary in order to provide an escape metabolic route, other features are needed to obtain drugs that are safe regarding DDI, TDP, and LFT elevations.

In addition to having two metabolic pathways, the drug should have a rapid metabolic clearance (short metabolic half-life) so that blood levels of unbound drug do not rise to dangerous levels in cases of DDI at the protein level. Also, if the metabolic half-life of the drug is too long, then the CYP450 system again becomes the main elimination pathway, thus defeating the original purpose of the design. In order to avoid high peak concentrations and rapidly declining blood levels when administered, such a drug should also be administered using a delivery system that produces constant and controllable blood levels over time.

The compounds of this invention have one or more of the following characteristics or properties:

1. Compounds of the invention are metabolized both by CYP450 and by a non-oxidative metabolic enzyme or system of enzymes;

2. Compounds of the invention have a short (up to four (4) hours) non-oxidative metabolic half-life;

3. Oral bioavailability of the compounds is consistent with oral administration using standard pharmaceutical oral formulations; however, the compounds, and compositions thereof, can also be administered using any delivery system that produces constant and controllable blood levels over time;

4. Compounds according to the invention contain a hydrolysable bond that can be cleaved non-oxidatively by hydrolytic enzymes;

5. Compounds of the invention can be made using standard techniques of small-scale and large-scale chemical synthesis;

6. The primary metabolites of compounds of this invention results from the non-oxidative metabolism of the compounds;

7. The primary metabolites, regardless of the solubility properties of the parent drug, is, or are, soluble in water at physiological pH and have, as compared to the parent compound, a significantly reduced pharmacological activity;

8. The primary metabolites, regardless of the electrophysiological properties of the parent drug, has, or have, negligible inhibitory activity at the $IK_R$ (HERG) channel at normal therapeutic concentration of the parent drug in plasma (e.g., the concentration of the metabolite must be at least five times higher than the normal therapeutic concentration of the parent compound before activity at the $IK_R$ channel is observed);

9. Compounds of the invention, as well as the metabolites thereof, do not cause metabolic DDI when co-administered with other drugs;

10. Compounds of the invention, as well as metabolites thereof, do not elevate LFT values when administered alone.

In some embodiments, the subject invention provides compounds have any two of the above-identified characteristics or properties. Other embodiments provide for compounds having at least any three of the above-identified properties or characteristics. In another embodiment, the compounds, and compositions thereof, have any combination of at least four of the above-identified characteristics or properties. Another embodiment provides compounds have any combination of five to 10 of the above-identified characteristics or properties. In a preferred embodiment the compounds of the invention have all ten characteristics or properties.

In various embodiments, the primary metabolites of the inventive compounds, regardless of the electrophysiological properties of the parent drug, has, or have, negligible inhibitory activity at the $IK_R$ (HERG) channel at normal therapeutic concentrations of the drug in plasma. In other words, the concentration of the metabolite can be at least five times higher than the normal therapeutic concentration of the parent compound before activity at the $IK_R$ channel is observed. Preferably, the concentration of the metabolite is at least ten times higher than the normal therapeutic concentration of the parent compound before activity at the $IK_R$ channel is observed.

Compounds according to the invention are, primarily, metabolized by endogenous hydrolytic enzymes via hydrolysable bonds engineered into their structures. The primary metabolites resulting from this metabolic pathway are water soluble and do not have, or show a reduced incidence of, DDI when administered with other medications (drugs). Non-limiting examples of hydrolysable bonds that can be incorporated into compounds according to the invention include amide, ester, carbonate, phosphate, sulfate, urea, urethane, glycoside, or other bonds that can be cleaved by hydrolases.

Additional modifications of the compounds disclosed herein can readily be made by those skilled in the art. Thus, analogs and salts of the exemplified compounds are within the scope of the subject invention. With a knowledge of the compounds of the subject invention skilled chemists can use known procedures to synthesize these compounds from available substrates. As used in this application, the term "analogs" refers to compounds which are substantially the same as another compound but which may have been modified by, for example, adding additional side groups. The term "analogs" as used in this application also may refer to compounds which are substantially the same as another compound but which have atomic or molecular substitutions at certain locations in the compound.

Analogs of the exemplified compounds can be readily prepared using commonly known, standard reactions. These standard reactions include, but are not limited to, hydrogenation, methylation, acetylation, and acidification reactions. For example, new salts within the scope of the invention can be made by adding mineral acids, e.g., HCl $H_2SO_4$, etc., or strong organic acids, e.g., formic, oxalic, etc., in appropriate amounts to form the acid addition salt of the parent compound or its derivative. Also, synthesis type reactions may be used pursuant to known procedures to add or modify various groups in the exemplified compounds to produce other compounds within the scope of the invention.

In a preferred embodiment, the subject invention provides compounds having Formula I:

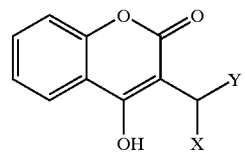

Formula I

Wherein:
X is independently in each occurrence hydrogen, alkyl, cycloalkyl, heterocyclyl, hydroxy, alkoxy, heteroaryl or aryl optionally substituted with $COOR_1$ or $R_2$.

$R_1$ is independently in each occurrence hydrogen, alkyl or alkylaryl, all optionally substituted with lower alkyl, hydroxy, or alkoxy.

$R_2$ is

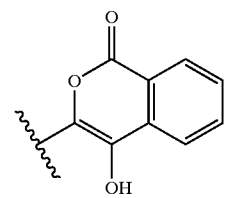

Y is independently in each occurrence $(CHR_3)_n COOR4$ or aryl optionally substituted with $COOR_5$, wherein n=1 to 3.

$R_3$ is independently in each occurrence hydrogen, alkyl or alkylaryl, aryl all optionally substituted with lower alkyl, hydroxy, or alkoxy.

$R_4$ is independently in each occurrence hydrogen, alkyl or alkylaryl, aryl all optionally substituted with lower alkyl, hydroxy, or alkoxy.

$R_5$ is independently in each occurrence hydrogen, alkyl or alkylaryl, aryl all optionally substituted with lower alkyl, hydroxy, or alkoxy.

X and Y taken together can form butyrolactone when X is OH and Y is O-benzoic acid.

Reference herein to "lower alkyl" refers to $C_{1-8}$ alkyl. As used herein, "aryl" refers to any aromatic group.

Specifically exemplified herein are the following compounds:

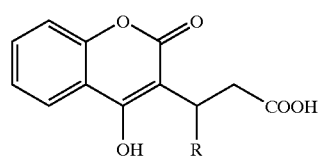

Formula II 3-(4-Hydroxy-2-oxo-2H-chromen-3-yl)-3-phenyl-propionic acid
3-(4-Hydroxy-2-oxo-2H-chromen-3-yl)-3-phenyl-propionic acid methyl ester
3-(4-Hydroxy-2-oxo-2H-chromen-3-yl)-3-phenyl-propionic acid ethyl ester
3-(4-Hydroxy-2-oxo-2H-chromen-3-yl)-3-phenyl-propionic acid n-propyl ester
3-(4-Hydroxy-2-oxo-2H-chromen-3-yl)-3-phenyl-propionic acid n-butyl ester
3-(4-Hydroxy-2-oxo-2H-chromen-3-yl)3-phenyl-propionic acid 2-butyl ester
3-(4-Hydroxy-2-oxo-2H-chromen-3-yl)-3-phenyl-propionic acid isopropyl ester 3-Cyclohexyl-3-(4-hydroxy-2-oxo-2H-chromen-3-yl)-propionic acid
3-Cyclohexyl-3-(4-hydroxy-2-oxo-2H-chromen-3-yl)-propionic acid methyl ester
3-Cyclohexyl-3-(4-hydroxy-2-oxo-2H-chromen-3-yl)-propionic acid ethyl ester
3-Cyclohexyl-3-(4-hydroxy-2-oxo-2H-chromen-3-yl)-propionic acid n-propyl ester
3-Cyclopentyl-3-(4-hydroxy-2-oxo-2H-chromen-3-yl)-propionic acid
3-Cyclopentyl-3-(4-hydroxy-2-oxo-2H-chromen-3-yl)-propionic acid methyl ester
3-Cyclopentyl-3-(4-hydroxy-2-oxo-2H-chromen-3-yl)-propionic acid ethyl ester
3-Cyclopentyl-3-(4-hydroxy-2-oxo-2H-chromen-3-yl)-propionic acid n-propyl ester
3-Propyl-3-(4-hydroxy-2-oxo-2H-chromen-3-yl)-propionic acid
3-Propyl-3-(4-hydroxy-2-oxo-2H-chromen-3-yl)-propionic acid methyl ester
3-Propyl-3-(4-hydroxy-2-oxo-2H-chromen-3-yl)-propionic acid ethyl ester
3-Propyl-3-(4-hydroxy-2-oxo-2H-chromen-3-yl)-propionic acid n-propyl ester

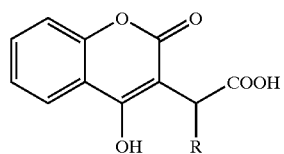

Formula III

4-Hydroxy-2-oxo-2H-chromen-3-yl)-phenyl-acetic acid
(4-Hydroxy-2-oxo-2H-chromen-3-yl)-phenyl-acetic acid methyl ester
(4-Hydroxy-2-oxo-2H-chromen-3-yl)-phenyl-acetic acid ethyl ester
(4-Hydroxy-2-oxo-2H-chromen-3-yl)-phenyl-acetic acid n-propyl ester
(4-Hydroxy-2-oxo-2H-chromen-3-yl)-phenyl-acetic acid 2-propyl ester
(4-Hydroxy-2-oxo-2H-chromen-3-yl)-phenyl-acetic acid n-butyl ester
2-(4-Hydroxy-2-oxo-2H-chromen-3-yl)-butyric acid
2-(4-Hydroxy-2-oxo-2H-chromen-3-yl)-butyric acid methyl ester
2-(4-Hydroxy-2-oxo-2H-chromen-3-yl)-butyric acid ethyl ester
2-(4-Hydroxy-2-oxo-2H-chromen-3-yl)-butyric acid n-propyl ester
2-(4-Hydroxy-2-oxo-2H-chromen-3-yl)-butyric acid isopropyl ester
2-(4-Hydroxy-2-oxo-2H-chromen-3-yl)-butyric acid n-butyl ester

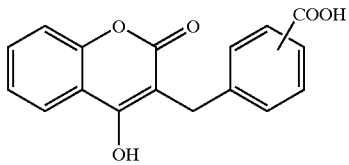

Formula IV 4-(4-Hydroxy-2-oxo-2H-chromen-3-ylmethyl)-benzoic acid
4-(4-Hydroxy-2-oxo-2H-chromen-3-ylmethyl)-benzoic acid methyl ester
4-(4-Hydroxy-2-oxo-2H-chromen-3-ylmethyl)-benzoic acid ethyl ester
4-(4-Hydroxy-2-oxo-2H-chromen-3-ylmethyl)-benzoic acid n-propyl ester
4-(4-Hydroxy-2-oxo-2H-chromen-3-ylmethyl)-benzoic acid n-butyl ester
2-(4-Hydroxy-2-oxo-2H-chromen-3-ylmethyl)-benzoic acid
2-(4-Hydroxy-2-oxo-2H-chromen-3-ylmethyl)-benzoic acid methyl ester
2-(4-Hydroxy-2-oxo-2H-chromen-3-ylmethyl)-benzoic acid ethyl ester
2-(4-Hydroxy-2-oxo-2H-chromen-3-ylmethyl)-benzoic acid n-propyl ester
2-(4-Hydroxy-2-oxo-2H-chromen-3-ylmethyl)-benzoic acid n-butyl ester
3-(4-Hydroxy-2-oxo-2H-chromen-3-ylmethyl)-benzoic acid
3-(4-Hydroxy-2-oxo-2H-chromen-3-ylmethyl)-benzoic acid methyl ester
3-(4-Hydroxy-2-oxo-2H-chromen-3-ylmethyl)-benzoic acid ethyl ester
3-(4-Hydroxy-2-oxo-2H-chromen-3-ylmethyl)-benzoic acid n-propyl ester
3-(4-Hydroxy-2-oxo-2H-chromen-3-ylmethyl)-benzoic acid n-butyl ester

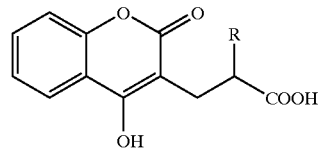

Formula V

2-Benzyl-3-(4-hydroxy-2-oxo-2H-chromen-3-yl)-propionic acid
2-Benzyl-3-(4-hydroxy-2-oxo-2H-chromen-3-yl)-propionic acid methyl ester
2-Benzyl-3-(4- hydroxy-2-oxo-2H-chromen-3-yl)-propionic acid ethyl ester
2-Benzyl-3-(4-hydroxy-2-oxo-2H-chromen-3-yl)-propionic acid n-propyl ester
2-Benzyl-3-(4-hydroxy-2-oxo-2H-chromen-3-yl)-propionic acid n-butyl ester
2-(4-Hydroxy-2-oxo-2H-chromen-3-ylmethyl)-butyric acid
2-(4-Hydroxy-2-oxo-2H-chromen-3-ylmethyl)-butyric acid methyl ester
2-(4-Hydroxy-2-oxo-2H-chromen-3-ylmethyl)-butyric acid ethyl ester
2-(4-Hydroxy-2-oxo-2H-chromen-3-ylmethyl)-butyric acid n-propyl ester
2-(4-Hydroxy-2-oxo-2H-chromen-3-ylmethyl)-butyric acid n-butyl ester

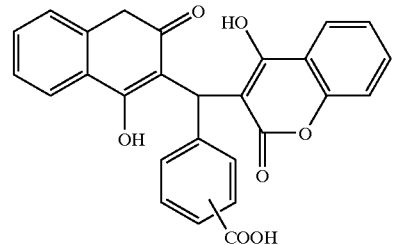

Formula VI

4-[(4-Hydroxy-2-oxo-2H-chromen-3-yl)(4-hydroxy-1-oxo-1H-isochromen-3-yl)-methyl]-benzoic acid
4-[(4-Hydroxy-2-oxo-2H-chromen-3-yl)(4-hydroxy-1-oxo-1H-isochromen-3-yl)-methyl]-benzoic acid methyl ester 4-[(4-Hydroxy-2-oxo-2H-chromen-3-yl)-(4-hydroxy-1-oxo-1H-isochromen-3-yl)-methyl]-benzoic acid ethyl ester 4-[(4-Hydroxy-2-oxo-2H-chromen-3-yl)-(4-hydroxy-1-oxo-1H-isochromen-3-yl)-methyl]-benzoic acid n-propyl ester 4-[(4-Hydroxy-2-oxo-2H-chromen-3-yl)-(4-hydroxy-1-oxo-1H-isochromen-3-yl)-methyl]-benzoic acid n-butyl ester 3-[(4-Hydroxy-2-oxo-2H-chromen-3-yl)-(4-hydroxy-1-oxo-1H-isochromen-3-yl)-methyl]-benzoic acid 3-[(4-Hydroxy-2-oxo-2H-chromen-3-yl)-(4-hydroxy-1-oxo-1H-isochromen-3-yl)-methyl]-benzoic acid methyl ester 3-[(4-Hydroxy-2-oxo-2H-chromen-3-yl)-(4-hydroxy-1-oxo-1H-isochromen-3-yl)-methyl]-benzoic acid ethyl ester 3-[(4-Hydroxy-2-oxo-2H-chromen-3-yl)-(4-hydroxy-1-oxo-1H-isochromen-3-yl)-methyl]-benzoic acid n-propyl ester 3-[(4-Hydroxy-2-oxo-2Chromen-3-yl)-(4-hydroxy-1-oxo-1H-isochromen-3-yl)-methyl]-benzoic acid n-butyl ester 2-[(4-Hydroxy-2-oxo-2H-chromen-3-yl)-(4-hydroxy 1-oxo-1H-isochromen-3-yl)-methyl]-benzoic acid 2-[(4-Hydroxy-2-oxo-2H-chromen-3-yl)-(4-hydroxy-1-oxo-1H-isochromen-3-yl)-methyl]-benzoic acid methyl ester 2-[(4-Hydroxy-2-oxo-2H-chromen-3-yl-(4-hydroxy-1-oxo-1H-isochromen-3-yl)-methyl]-benzoic acid ethyl ester 2-[(4-Hydroxy-2-oxo-2H-chromen-3-yl)-(4-hydroxy-1-oxo-1H-isochromen-3-yl)-methyl]-benzoic acid n-propyl ester 2-[(4-Hydroxy-2-oxo-2H-chromen-3-yl)-(4-hydroxy-1-oxo-1H-isochromen-3-yl)-methyl]-benzoic acid n-butyl ester Formula VII

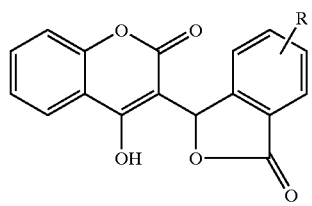

3-(1-Hydroxy-3-oxo-3,4-dihydro-naphthalen-2-yl)-3H-isobenzofuran-1-one

In Formulae II–VII "R" is defined consistent with the exemplified compounds, as well as the definition of "X" in Formula I.

The subject invention also provides processes for the manufacturing of novel coumarin derivatives. Examples of synthetic schemes are as follows:

Scheme 1 provides an exemplary synthesis of C-3 substituted 4-hydroxycoumarins. Appropriately substituted bromoacetate and 4-hydroxycoumarin in the presence of a base give mixture of O and C-3 alkylated 4-hydroxy coumarins, which are readily separable.

Scheme 2 provides an alternative synthesis of C-3 substituted 4-hydroxycoumarins when $R_1$ is aryl groups. 4-hydroxycoumarin and an aromatic aldehyde can be heated in a mixture of triethylamine and formic acid (2:5 molar ratio) to give 3-benzyl-4-hydroxycoumarin, which was in turn treated with 2.2 eq. of BuLi and quenched with carbon dioxide to give coumarin substituted phenyl-acetic acid. Corresponding esters can be obtained by treating the acid with various alcohols in the presence of concentrated sulfuric acid.

Scheme 3 illustrates the synthesis of chromen-3-yl-propionic acid. 4-hydroxycoumarin, an appropriate aldehyde and meldrum's acid can be heated in EtOH in the presence ammonium acetate to give substituted propionate, which can then be treated with 2 eq. of LDA and an alkylating agent to provide the chromen-3-yl-propionionates.

Scheme 1

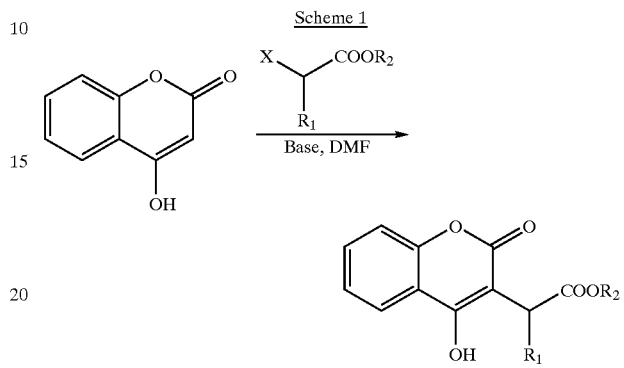

Scheme 2

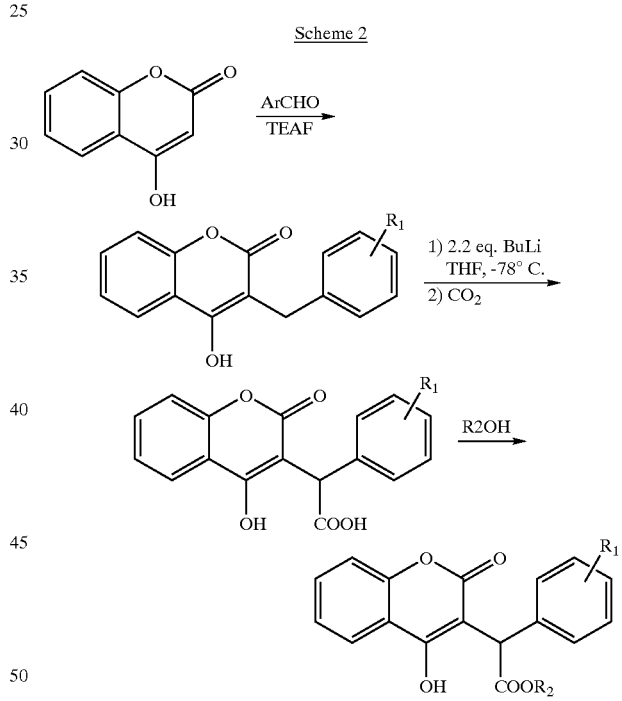

Scheme 3

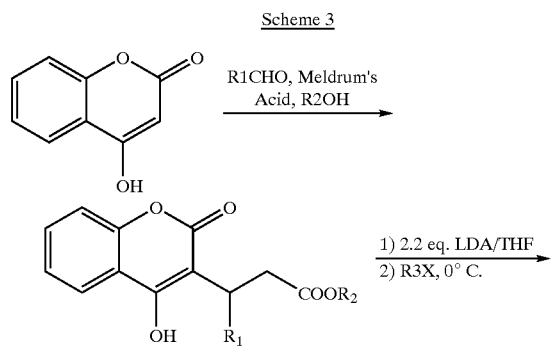

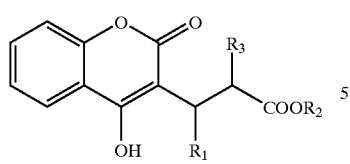

Exemplary reaction schemes for the production of derivatives of 7-hydroxycoumarin which have anti-coagulant properties are provided below. The synthesis of 4-Hydroxy-3-(3-methoxy-3-oxo-1-phenylpropyl)-2H-1-benzopyran-2-one 3 is performed by Michael condensation of 4-Hydroxycoumarin 1 and methyl trans-cinnamate 2 in absolute ethanol in the presence of sodium ethoxide at reflux temperature for 16 hours.

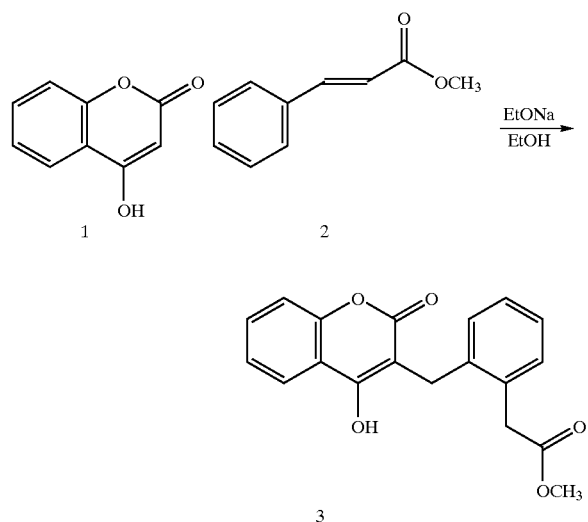

Knoevenagel reaction between 4-Hydroxycoumarin 1 and benzaldehyde 4 in the presence of piperidinium benzoate gives the benzal adduct 5. Michael addition between 5 and ethoxycarbonylmethyldimethylsulfide in toluene in the presence of DBU as a base gives the cyclopropane derivative 6. Michael addition between 5 and diethyl malonate in absolute ethanol with sodium ethoxide gives 7.

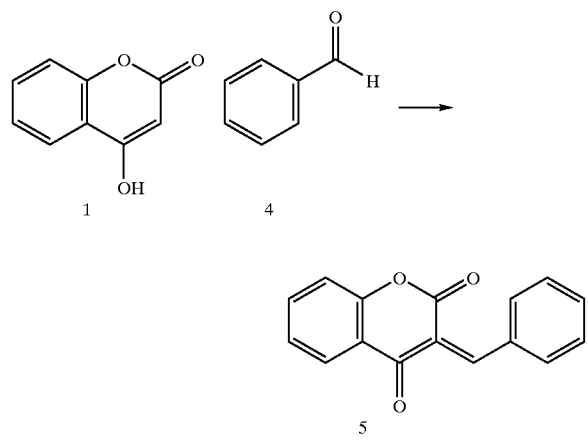

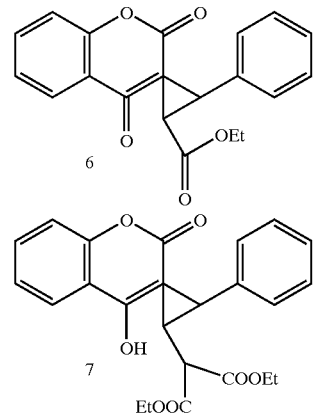

The subject invention further pertains to enantiomerically isolated compounds, and compositions comprising the compounds, for the treatment of coagulation disorders. The isolated enantiomeric forms of the compounds of the invention are substantially free from one another (i.e., in enantiomeric excess). In other words, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. In one embodiment of the invention, the isolated enantiomeric compounds are at least about in 80% enantiomeric excess. In a preferred embodiment, the compounds are in at least about 90% enantiomeric excess. In a more preferred embodiment, the compounds are in at least about 95% enantiomeric excess. In an even more preferred embodiment, the compounds are in at least about 97.5% enantiomeric excess. In a most preferred embodiment, the compounds are in at least 99% enantiomeric excess.

The subject invention also provides methods for treating coagulation disorders comprising the administration of a therapeutically effective amount of the esterified warfarin analogs of this invention to an individual in need of treatment. The wafarin analogs of this invention have applicability in both veterinary and human clinical contexts. Further, the compounds of this invention have therapeutic properties similar to those of the unmodified parent compound (COUMADINE). Accordingly, dosage rates and routes of administration of the disclosed compounds are similar to those already used in the art and known to the skilled artisan (see, for example, *Physicians' Desk Reference*, 54th Ed., Medical Economics Company, Montvale, N.J., 2000 or U.S. Pat. No. 5,856,525 hereby incorporated by reference in its entirety).

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as an active ingredient, an effective amount of one or more of the compounds and one or more non-toxic, pharmaceutically acceptable carrier or diluent. Examples of such carriers for use in the invention include ethanol, dimethyl sulfoxide, glycerol, silica, alumina, starch, and equivalent carriers and diluents.

Further, acceptable carriers can be either solid or liquid. Solid form preparations include powders, tablets, pills, capsules, cachets, suppositories and dispersible granules. A solid carrier can be one or more substances which may act as diluents, flavoring agents solubilizers, lubricants, suspending agents, binders, preservatives, tablet disintegrating agents or an encapsulating material.

The disclosed pharmaceutical compositions may be subdivided into unit doses containing appropriate quantities of the active component. The unit dosage form can be a packaged preparation, such as packeted tablets, capsules, and powders in paper or plastic containers or in vials or ampoules. Also, the unit dosage can be a liquid based preparation or formulated to be incorporated into solid food products, chewing gum, or lozenge.

The term "individual(s)" is defined as a single mammal to which is administered a compound of the present invention. The mammal may be a rodent, for example a mouse or rat, pig, horse, rabbit, goat, pig, cow, cat, dog, or human. In a preferred embodiment, the individual is a human.

Following are examples which illustrate procedures for practicing the invention. These examples should not be construed as limiting. All percentages are by weight and all solvent mixture proportions are by volume unless otherwise noted.

EXAMPLE 1

Preparation of 2-(4-Hydroxy-2-oxo-2H-chromen-3-yl)-butyric acid ethyl ester

To a solution of 4-hydroxy-chromen-2-one (2.0 g) and ethyl 2-bromobutyrate (2 mL) in DMF was added anhydrous potassium carbonate (8.5 g). The resulting reaction mixture was stirred at room temperature for 72 hours, then diluted with water and extracted with EtOAc. The organic layer was washed with saturated aqueous sodium bicarbonate, dried over MgSO4 and conc. in vacuo to provide colorless oil, which was purified by column chromatography to give 2-(4-Hydroxy-2-oxo-2H-chromen-3-yl)-butyric acid ethyl ester as a white solid, MS: 275[M-H].

EXAMPLE 2

Preparation of 2-Benzyl-3-(4-hydroxy-2-oxo-2H-chromen-3-yl)-propionic acid ethyl ester A solution of 4-hydroxy-chromen-2-one (2.0 g), aqueous formaldehyde (37%, 0.37 g), Meldrum's acid (1.77 g) and ammonium acetate (0.95 g) in ethanol (75 mL) was heated to reflux for 6 hours, then cooled to room temperature. The reaction mixture was conc. in vacuo to give the crude as yellow oil, which was purified by column chromatography to provide 3-(4-Hydroxy-2-oxo-2H-chromen-3-yl)-propionic acid ethyl ester as colorless oil (1.2 g).

To a solution of 3-(4-Hydroxy-2-oxo-2H-chromen-3-yl)-propionic acid ethyl ester in THF at −78° C. was added LDA (1.5M, 3.05 mL) dropwise. A yellow precipitate was formed during the addition. The reaction was stirred at −78° C. for 15 min and allowed to warmed to 0° C. and stirred for 30 min, after which BnBr (0.24 mL in THF) was added dropwise. The reaction was warmed to room temperature, stirred for 12 hours, cooled to 0° C. and quenched with saturated ammonium chloride and extracted with EtOAc. The organic layer was washed with brine, dried over MgSO4 and conc. in vacuo to a crude colorless oil, which was purified by column chromatography to provide 2-Benzyl-3-(4-hydroxy-2-oxo-2H-chromen-3-yl)-propionic acid ethyl ester as a colorless oil (250 mg). MS: 351 [M-H].

EXAMPLE 3

Preparation of 2-Benzyl-3-(4-hydroxy-2-oxo-2H-chromen-3-yl)-propionic acid

2-Benzyl-3-(4-hydroxy-2-oxo-2H-chromen-3-yl)-propionic acid ethyl ester (160 mg) in EtOH (1 mL) was added 1N NaOH (1.36 mL). The resulting mixture was heated to 50° C. and stirred for 2 hours, cooled to room temperature, acidified with Conc. HCl/ice and extracted with ether. The organic layer was dried over MgSO4 and conc. in vacuo to give 2-Benzyl-3-(4-hydroxy-2-oxo-2H-chromen-3-yl)-propionic acid as a pale yellow solid (120mg). MS: 323[M-H].

EXAMPLE 4

Preparation of (4-Hydroxy-2-oxo-2H-chromen-3-yl)-Phenyl-acetic acid ethyl ester

Triethylammonium formate (TEAF) was prepared by adding TEA (20.0 mL) to formic acid (16.5 mL) with ice cooling. To TEAF was added benzaldehyde (3.78 mL) and 4-hydroxy-chromen-2-one (6.0 g) and the resulting mixture was heated to 130–140° C. for 3 hours, cooled to room temperature, diluted with water, and extracted with EtOAc. The organic layer was washed with brine, dried over MgSO4 and conc. in vacuo to give a light yellow solid. The crude solid was recrystallized from EtOH to give 3-Benzyl-4-hydroxy-chromen-2-one as a white solid (1.95 g).

To a solution of 3-Benzyl-4-hydroxy-chromen-2-one (2.0 g) in THF at −78° C. was added BuLi (1.6M, 11.4 mL) dropwise during which a yellow precipitate was formed. The reaction was stirred at −78° C. for 30 min and carbon dioxide gas was bubbled through for 10 min, warmed to 0° C. and quenched with saturated ammonium chloride, extracted with EtOAc (3×50 mL). The aqueous phase was acidified with conc. HCl and extracted with EtOAc. The organic layer was dried over MgSO4 and conc. in vacuo to provide a colorless oil, which crystallize up standing to give (4-Hydroxy-2-oxo-2H-chromen-3-yl)-phenyl-acetic acid as a white solid (920mg). MS: 295[M-H].

A solution of (4-Hydroxy-2-oxo-2H-chromen-3-yl)-phenyl-acetic acid in EtOH with a catalytic amount of conc. sulfuric acid was heated to reflux for 5 hours, cooled to room temperature, diluted with water and extracted with EtOAc. The organic layer was dried over MgSO4 and conc. in vacuo to give (4-Hydroxy-2-oxo-2H-chromen-3-yl)-phenyl-acetic acid ethyl ester as colorless oil, which crystallize upon standing (910 mg). MS: 323[M-H].

EXAMPLE 5

Preparation of 4-Hydroxy-3-(3-oxo-1,3-dihydro-isobenzofuran-1-yl)-chromen-2-one

A solution of 4-hydroxy-chromen-2-one (650 mg) and 2-carboxybenzyladehyde (300 mg) in EtOH was heated to reflux for 4 hours, cooled to room temperature then concentrated in vacuo to give a crude oil, which was diluted with water. The precipitated 4-hydroxy-chromen-2-one was collected by filtration (490 mg). A second crop of solid was collected from the mother liquor and triturated with hot EtOAc and filtered to provide 4-Hydroxy-3-(3-oxo-1,3-dihydro-isobenzofuran-1-yl)-chromen-2-one as white solid. MS: 293 [M-H].

EXAMPLE 6

Preparation of 2-(4-Hydroxy-2-oxo-2H-chromen-3-ylmethyl)-benzoic acid methyl ester To a solution 4-Hydroxy-3-(3-oxo-1,3-dihydro-isobenzofuran-1-yl)-chromen-2-one (60mg) in ethanol was added 10% Pd/C (10 mg) then stirred under a hydrogen balloon for 12 hours. The reaction mixture was filtered through a pad of celite and the filtrate was concentrated in vacuo to give 2-(4-Hydroxy-2-oxo-2H-chromen-3-ylmethyl)-benzoic acid as white solid (50 mg). MS: 295[M-H].

A solution of 2-(4-Hydroxy-2-oxo-2H-chromen-3-ylmethyl)-benzoic acid in MeOH with a catalytic amount of conc. sulfuric acid was heated to reflux for 5 hours, cooled to room temperature, diluted with water and extracted with EtOAc. The organic layer was dried over MgSO4 and conc. in vacuo to give 2-(4-Hydroxy-2-oxo-2H-chromen-3-ylmethyl)-benzoic acid methyl ester as white solid. MS: 309[M-H].

EXAMPLE 7

Mice in vivo, Bleeding Time

Test substance was administered orally (30, 10 and 3 mg/kg) to a group of 3 ICR derived male or female mice weighing 22±2 grams, respectively, at 18, 24 and 30 hours before standardized transection of the tip (0.5 mm) of each tail. The mice, in holders, were immediately suspended vertically with the distal 2 cm of each tail immersed in a test tube containing saline at 37° C. The time required for beginning a 15 second period of bleeding cessation is then determined; a maximum cut-off time of 180 seconds is used. Prolongation of bleeding time by 50 percent or more (≧50%) relative to a control group of animals was considered significant.

EXAMPLE 8

Selected Compounds of the Subject Invention

The subject invention is demonstrated in the production of warfarin analogs which have been designed to be metabolized by esterase enzymes. Exemplary compounds include structures of the formula:

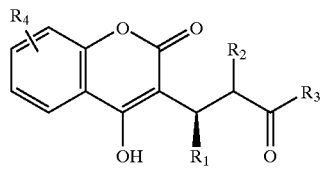

-continued

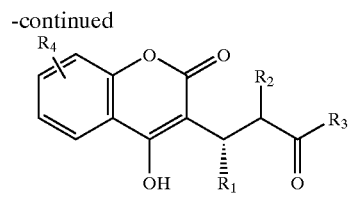

wherein
$R_1$ is selected from the group consisting of —$CH_2$—COO—$R_5$, —$CH(COOR_5)_2$;
$R_2$ is H;
$R_3$ is selected from the group consisting of $C_{1-4}$ alkyl, phenyl, and benzyl; and,
$R_4$ is H or a halogen; and,
$R_5$ is selected from the group consisting of $C_{1-4}$ alkyl, phenyl, and benzyl groups.

Other embodiments of this invention contemplate compounds of the formula:

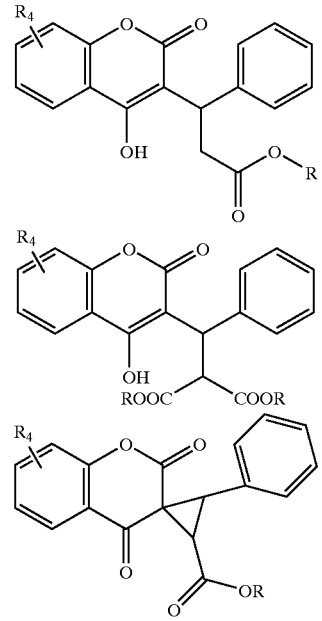

wherein R is selected from the group consisting of $C_{1-4}$ alkyl, phenyl, and benzyl groups and $R_4$ is defined as above, H or a halogen.

Modifications of the compounds disclosed herein can readily be made by those skilled in the art. Thus, analogs, derivatives, and salts of the exemplified compounds are within the scope of the subject invention. With a knowledge of the compounds of the subject invention, and their structures, skilled chemists can use known procedures to synthesize these compounds from available substrates.

All patents, patent applications, provisional applications, and publications referred to or cited herein are incorporated by reference in their entirety, including all figures and tables, to the extent they are not inconsistent with the explicit teachings of this specification. Any compounds specifically disclosed in Synthetic Communications Journal (1993) 25:631–640 are specifically excluded from the scope of the compounds of the subject invention.

It should be understood that the examples and embodiments described herein are for illustrative purposes only and that various modifications or changes in light thereof will be suggested to persons skilled in the art and are to be included within the spirit and purview of this application.

We claim:

1. An anticoagulant compound, having the following formula, including salts and isomers:

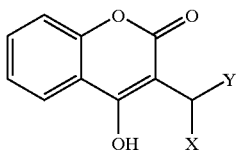

Formula I wherein
X is hydrogen, alkyl, cycloalkyl, heterocyclyl, hydroxy, alkoxy, or heteroaryl or aryl optionally substituted with $COOR_1$;
$R_1$ is hydrogen, alkyl or alkylaryl, all optionally substituted with lower alkyl, hydroxy, or alkoxy;
Y is $(CHR_3)_n COOR_4$ or aryl substituted with $COOR_5$, wherein n=1–3;
$R_3$ is hydrogen, alkyl, alkylaryl, or aryl all optionally substituted with lower allyl, hydroxy, or alkoxy;
$R_4$ is alkyl, alkylaryl, or aryl all optionally substituted with lower alkyl, hydroxy, or alkoxy; and
$R_5$ is hydrogen, alkyl, alkylaryl, or aryl all optionally substituted with lower alkyl, hydroxy, or alkoxy.

2. The compound, according to claim 1, wherein X is hydrogen, alkyl, cycloalkyl, heterocyclyl, hydroxy, alkoxy, heteroaryl or aryl optionally substituted with $COOR_1$; $R_1$ is hydrogen, alkyl or alkylaryl, all optionally substituted with lower alkyl, hydroxy, or alkoxy; and Y is $CH_2 COOR_4$.

3. The compound, according to claim 1, wherein X is hydrogen and Y is aryl substituted with $COOR_5$.

4. The compound, according to claim 1, having one of the following structures:

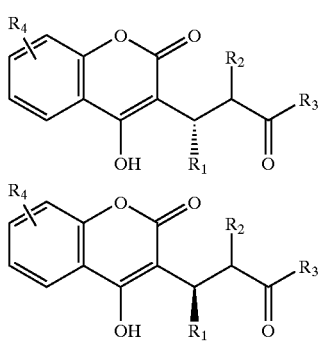

wherein
$R_1$ is selected from the group consisting of $CH_2COOR_5$, $CH(COOR_5)_2$;
$R_2$ is H;
$R_3$ is selected from the group consisting of $C_{1-4}$ alkyl, phenyl, and benzyl;
$R_4$ is H or a halogen; and,
$R_5$ is selected from the group consisting of $C_{1-4}$ alkyl, phenyl, and benzyl groups.

5. A pharmaceutical composition, comprising a pharmaceutical carrier and a compound having the following formula, including salts and isomers:

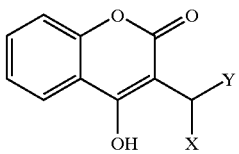

wherein
X is hydrogen, alkyl, cycloalkyl, heterocyclyl, hydroxy, alkoxy, or heteroaryl or aryl optionally substituted with $COOR_1$;
$R_1$ is hydrogen, alkyl or alkylaryl, all optionally substituted with lower alkyl, hydroxy, or alkoxy;
Y is $(CH_3)_n COOR_4$ or aryl substituted with $COOR_5$, wherein n=1–3;
$R_3$ is hydrogen, alkyl, alkylaryl, or aryl all optionally substituted with lower alkyl, hydroxy, or alkoxy;
$R_4$ is alkyl, alkylaryl, or aryl all optionally substituted with lower alkyl, hydroxy, or alkoxy, and
$R_5$ is hydrogen, alkyl, alkyaryl, or aryl all optionally substituted with lower alkyl, hydroxy, or alkoxy; or.

6. The composition, according to claim 5, having the following structure:

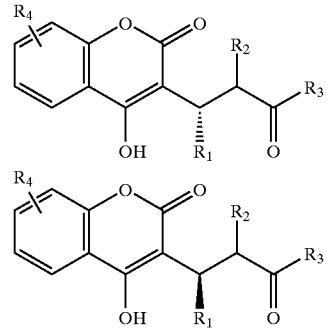

wherein
$R_1$ is selected from the group consisting of $CH_2COOR_5$, $CH(COOR_5)_2$;
$R_2$ is H;
$R_3$ is selected from the group consisting of $C_{1-4}$ alkyl, phenyl, and benzyl; and,
$R_4$ is H or a halogen; and,
$R_5$ is selected from the group consisting of $C_{1-4}$ alkyl, phenyl, and benzyl groups.

7. A method, for providing anticoagulant activity to a patient in need of such activity, wherein said method comprises administering to a patient in need of such treatment a compound having the following formula, including salts and isomers:

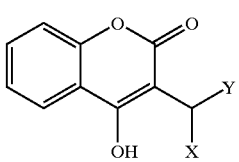

wherein
X is hydrogen, alkyl, cycloalkyl, heterocyclyl, hydroxy, alkoxy, or heteroaryl or aryl optionally substituted with $COOR_1$;

$R_1$ is hydrogen, alkyl or alkylaryl, all optionally substituted with lower alkyl, hydroxy, or alkoxy;

Y is $(CHR_3)_n COOR_4$ or aryl substituted with $COOR_5$, wherein n=1–3;

$R_3$ is hydrogen, alkyl, alkylaryl, or aryl all optionally substituted with lower alkyl, hydroxy, or alkoxy;

$R_4$ is alkyl, alkylaryl, or aryl all optionally substituted with lower alkyl, hydroxy, or alkoxy; and $R_5$ is hydrogen, alkyl, alkylaryl, or aryl all optionally substituted with lower alkyl, hydroxy, or alkoxy.

8. The method, according to claim 7, comprising administering a compound having the following structure:

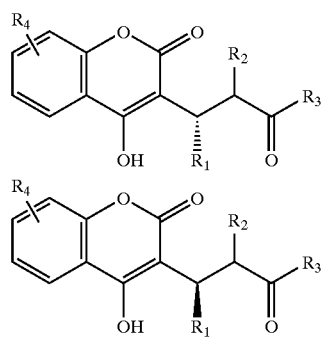

wherein $R_1$ is selected from the group consisting of $CH_2COOR_5$, $CH(COOR_5)_2$;

$R_2$ is H;

$R_3$ is selected from the group consisting of $C_{1-4}$ alkyl, phenyl, and benzyl; and, $R_4$ is H or a halogen; and, $R_5$ is selected from the group consisting of $C_{1-4}$ alkyl, phenyl, and benzyl groups.

9. The method, according to claim 7, wherein the patient is a human.

10. An anticoagulant compound, having the following formula, including salts and isomers:

Formula I

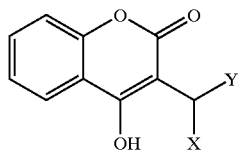

wherein:

X is hydrogen; and

Y is aryl substituted with $COOR_1$, wherein $R_1$ is a substituted or unsubstituted alkyl.

11. An anticoagulant compound, having the following formula, including salts and isomers:

Formula I

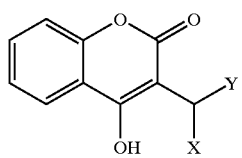

wherein:

X is aryl substituted with more than one substituent or with a substituted alkoxy;

Y is $(CHR_3)_n COOR_4$, wherein n=1–3;

$R_3$ is hydrogen, or a substituted or unsubstituted alkyl; and $R_4$ is hydrogen, or a substituted or unsubstituted alkyl.

12. A pharmaceutical composition, comprising a pharmaceutical carrier and a compound having the following formula, including salts and isomers:

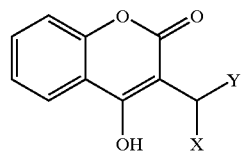

wherein:

X is hydrogen; and

Y is aryl substituted with $COOR_1$, wherein $R_1$ is a substituted or unsubstituted alkyl.

13. A pharmaceutical composition, comprising a pharmaceutical carrier and a compound having the following formula, including salts and isomers:

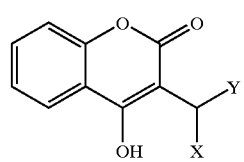

wherein

X is aryl substituted with more than one substituent or with a substituted alkoxy, Y is $(CHR_3)_n COOR_4$, wherein=1–3;

$R_3$ is hydrogen, or a substituted or unsubstituted allyl; and $R_4$ is hydrogen, or a substituted or unsubstituted alkyl.

14. A method, for providing anticoagulant activity to a patient in need of such activity, wherein said method comprising administering to a patient in need of such treatment a compound having the following formula, including salts and isomers:

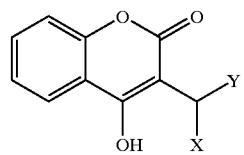

wherein:

X is hydrogen; and

Y is aryl substituted with $COOR_1$, wherein $R_1$ is a substituted or unsubstituted alkyl.

15. A method, for providing anticoagulant activity to a patient in need of such activity, wherein said method comprising administering to a patient in need of such treatment a compound having the following formula, including salts and isomers:

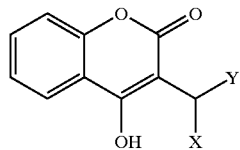
wherein:
X is aryl substituted with more t an one substituent or with a substituted alkoxy,
Y is $(CHR_3)_n\ COOR_4$, wherein n=1–3;
$R_3$ is hydrogen, or a substituted or unsubstituted alkyl; and
$R_4$ is hydrogen, or a substituted or unsubstituted alkyl.
* * * * *